(12) United States Patent
Oh

(10) Patent No.: US 11,426,510 B2
(45) Date of Patent: Aug. 30, 2022

(54) MEDICAL DEVICE FOR CONSTIPATION PREVENTION, COPROSTASIS REMOVAL AND GOOD BOWEL MOVEMENT

(71) Applicant: Young Kuk Oh, Seoul (KR)

(72) Inventor: Young Kuk Oh, Seoul (KR)

(*) Notice: Subject to any disclaimer, the term of this patent is extended or adjusted under 35 U.S.C. 154(b) by 779 days.

(21) Appl. No.: 16/348,051

(22) PCT Filed: Nov. 14, 2018

(86) PCT No.: PCT/KR2018/013870
§ 371 (c)(1),
(2) Date: May 7, 2019

(87) PCT Pub. No.: WO2020/096106
PCT Pub. Date: May 14, 2020

(65) Prior Publication Data
US 2020/0316286 A1 Oct. 8, 2020

(30) Foreign Application Priority Data
Nov. 5, 2018 (KR) .................. 10-2018-0134306

(51) Int. Cl.
*A61M 3/02* (2006.01)
*A61M 39/22* (2006.01)
(Continued)

(52) U.S. Cl.
CPC ............ *A61M 3/025* (2013.01); *A61M 3/022* (2014.02); *A61M 3/0216* (2014.02);
(Continued)

(58) Field of Classification Search
CPC ...... A61M 2039/226; A61M 2202/068; A61M 2205/0205; A61M 2205/7545; A61M 2210/1064; A61M 2210/1475; A61M 39/22; A61M 3/0216; A61M 3/022; A61M 3/025; A61M 3/0279; B01D 2201/16; B01D 2201/309; B01D 35/06; B01D 35/20; C02F 1/003; C02F 1/34; C02F 1/482;
(Continued)

(56) References Cited

U.S. PATENT DOCUMENTS 5,795,471 A * 8/1998 Naito ..................... C02F 1/285
210/283
8,967,499 B2 * 3/2015 Lee ....................... B05B 15/40
239/461

FOREIGN PATENT DOCUMENTS

KR 10-2009-0055296 A 6/2009
KR 10-0966472 B1 6/2010
(Continued)

*Primary Examiner* — Terry K Cecil
(74) *Attorney, Agent, or Firm* — David Millers

(57) ABSTRACT

A medical device includes: a hollow body part formed in a predetermined bent shape; a head part provided at a tip portion thereof with a discharge port for discharging cleaning water and detachably coupled to a front end of the body part; a connection part connected to a shower hose and a rear end of the body part and provided with a control valve for controlling water supply, a water flow rate and a water pressure; a water purification tube built in the body part and provided with leakage preventing grilles at both ends thereof; and a purified water discharge part provided inside the head part and configured to remove foreign substances in the water by using a filter.

8 Claims, 8 Drawing Sheets

(51) Int. Cl.
  *B01D 35/06* (2006.01)
  *B01D 35/20* (2006.01)
  *C02F 9/00* (2006.01)
  *C02F 1/00* (2006.01)
  *C02F 1/34* (2006.01)
  *C02F 1/48* (2006.01)
  *C02F 1/50* (2006.01)
  *C02F 101/10* (2006.01)

(52) U.S. Cl.
  CPC .............. *A61M 39/22* (2013.01); *B01D 35/06* (2013.01); *B01D 35/20* (2013.01); *C02F 9/005* (2013.01); *A61M 2039/226* (2013.01); *A61M 2202/068* (2013.01); *A61M 2205/0205* (2013.01); *A61M 2205/7545* (2013.01); *A61M 2210/1064* (2013.01); *A61M 2210/1475* (2013.01); *B01D 2201/16* (2013.01); *B01D 2201/309* (2013.01); *C02F 1/003* (2013.01); *C02F 1/34* (2013.01); *C02F 1/482* (2013.01); *C02F 1/50* (2013.01); *C02F 2101/10* (2013.01); *C02F 2201/005* (2013.01); *C02F 2209/40* (2013.01); *C02F 2303/04* (2013.01); *C02F 2307/06* (2013.01)

(58) Field of Classification Search
  CPC .. C02F 1/50; C02F 2101/10; C02F 2201/005; C02F 2209/40; C02F 2303/04; C02F 2307/06; C02F 9/005
  See application file for complete search history.

(56) References Cited

FOREIGN PATENT DOCUMENTS

| | | | |
|---|---|---|---|
| KR | 10-2016-0018057 A | 2/2016 | |
| KR | 10-1953137 B1 | 2/2019 | |
| WO | WO-2006049071 A1 * | 5/2006 | ............. A61H 33/04 |

* cited by examiner

[FIG.1]
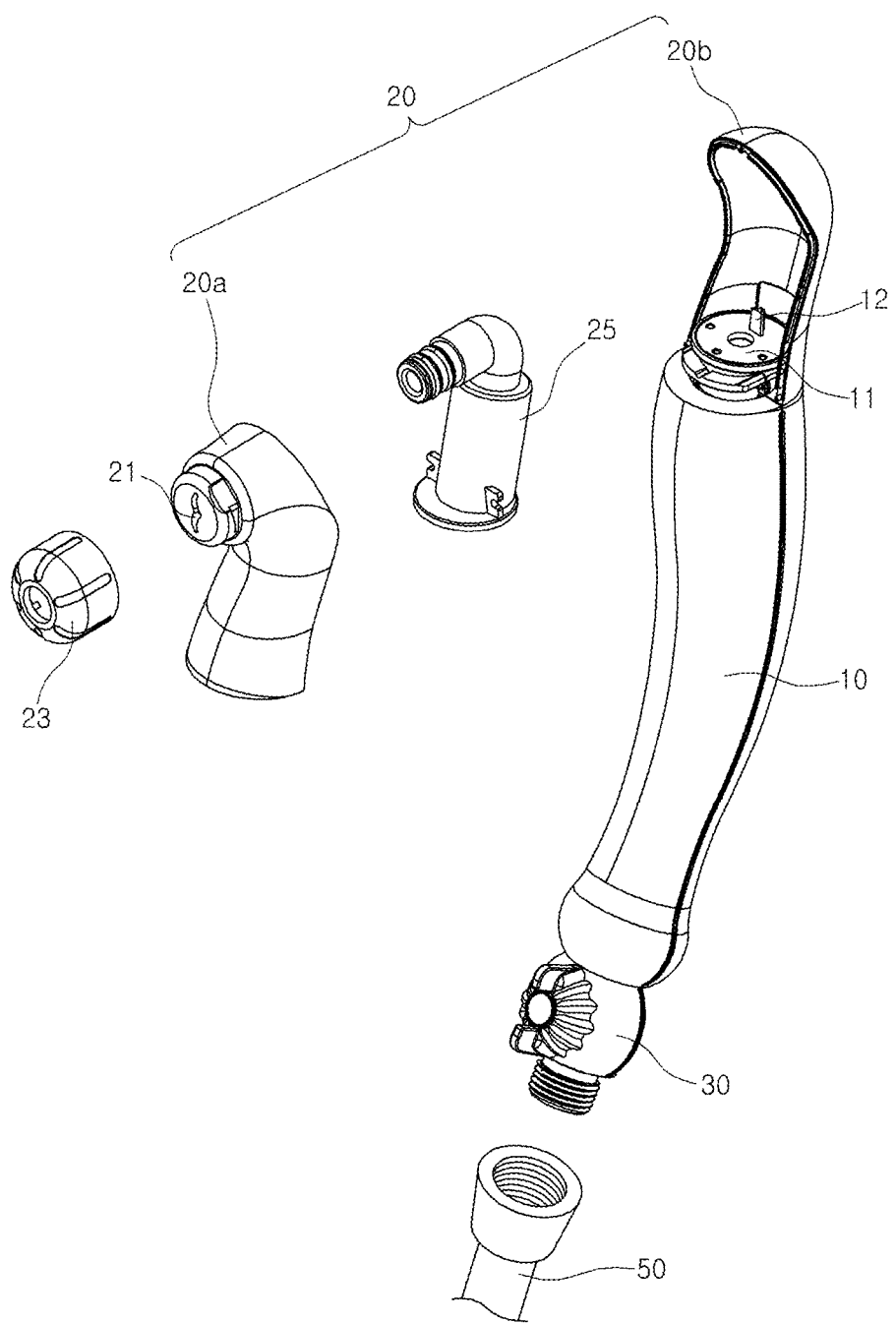

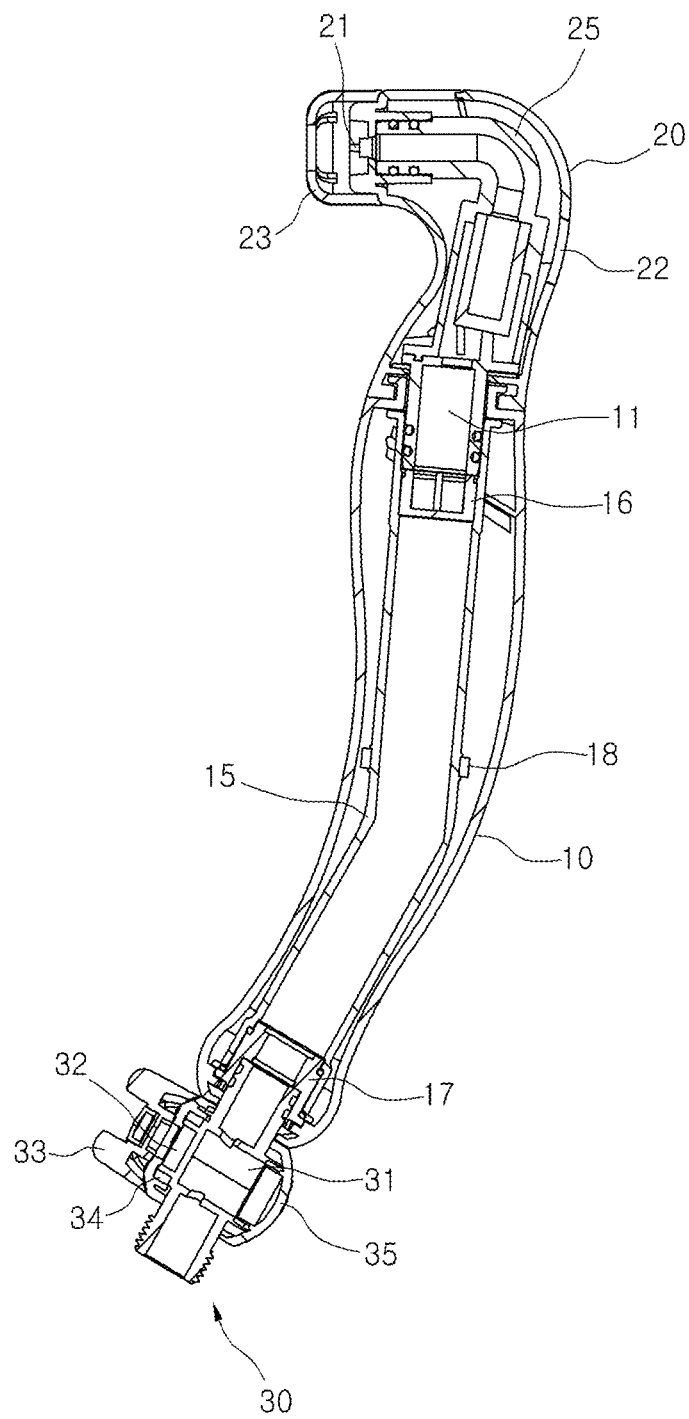
[Fig. 2]

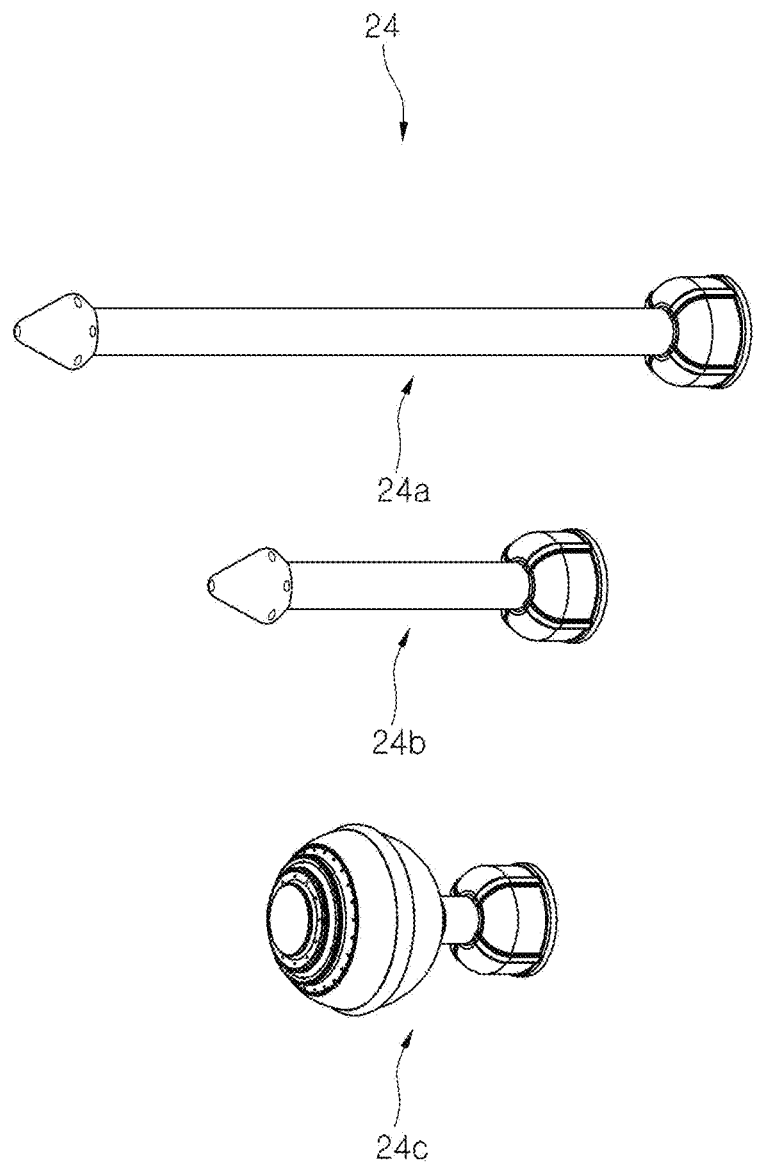

[FIG.4]
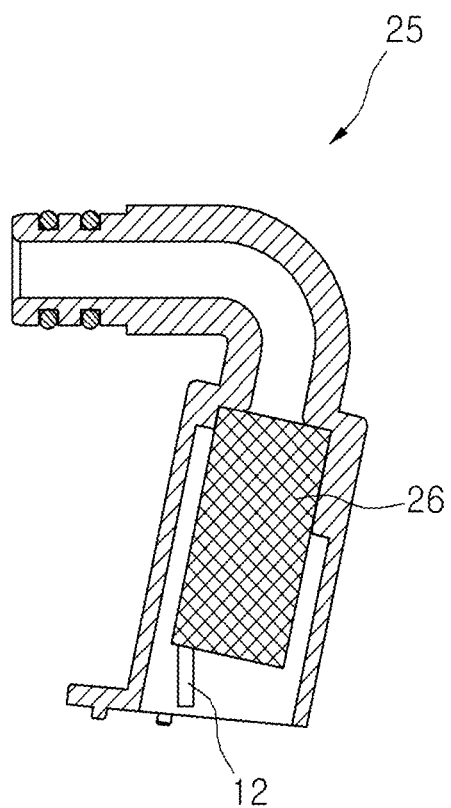

[FIG.5]
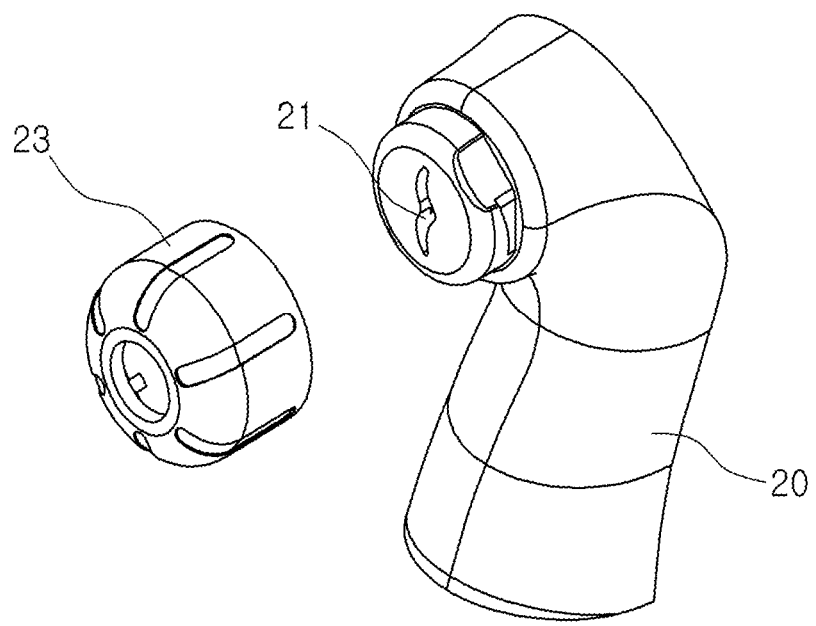

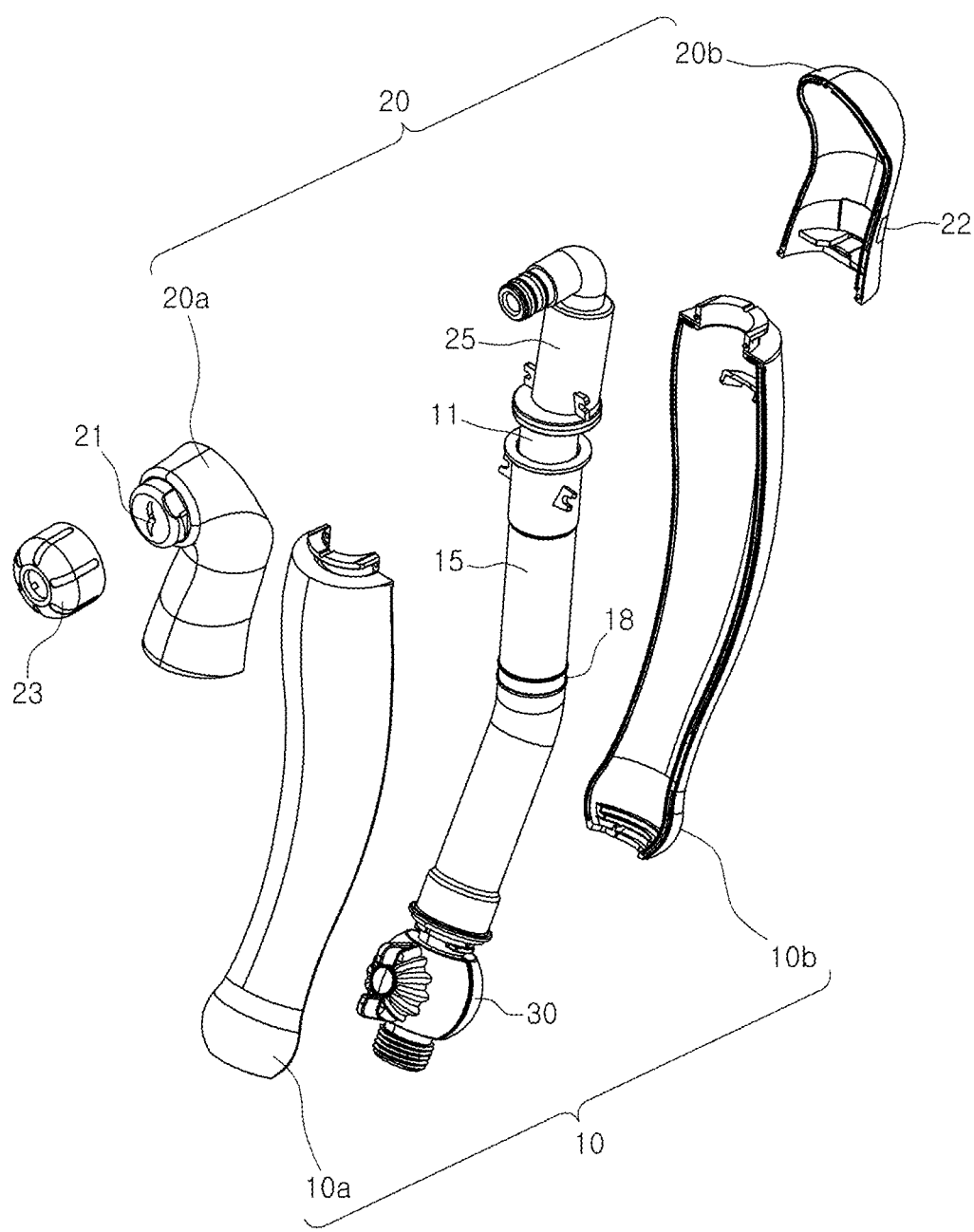
[Fig. 6]

[FIG.7]
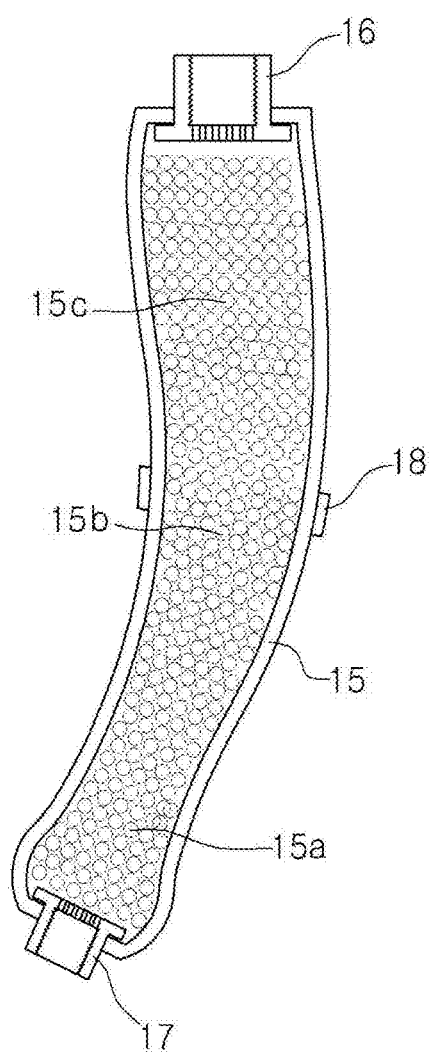

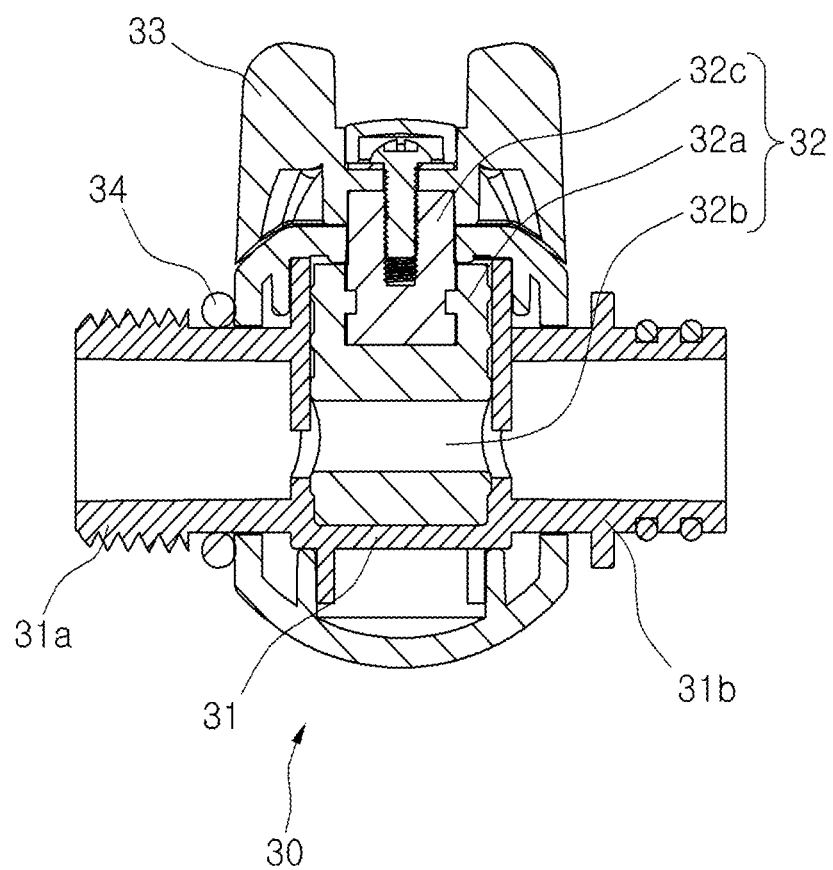
[FIG.8]

MEDICAL DEVICE FOR CONSTIPATION PREVENTION, COPROSTASIS REMOVAL AND GOOD BOWEL MOVEMENT

CROSS-REFERENCE TO RELATED APPLICATIONS

The present application is a § 371 application of International Application No. PCT/KR2018/013870 filed on Nov. 14, 2018 and entitled "MEDICAL DEVICE FOR CONSTIPATION PREVENTION, COPROSTASIS REMOVAL AND GOOD BOWEL MOVEMENT," which claims the benefit of Korean Patent Application No. 10-2018-0134306 filed on Nov. 5, 2018. International Application No. PCT/KR2018/013870 and Korean Patent Application No. 10-2018-0134306 are incorporated herein.

TECHNICAL FIELD

The present invention relates to a medical device for constipation prevention, coprostasis removal and good bowel movement and, more particularly, to a medical device for constipation prevention, coprostasis removal and good bowel movement, which is capable of being detachably attached to a shower hose, capable of discharging purified functional water to clean the inside of a colon or a vagina and capable of being used as an anus-cleaning bidet or an ordinary shower device.

BACKGROUND ART

In recent years, there are many cases where a bidet device for spraying water to an anus or a local area is installed in a toilet seat.

The bidet device is capable of keeping an anus and a local area clean and preventing disease. Therefore, the bidet device is increasingly used.

The ordinary bidet device installed at the toilet seat is configured to spray water toward the anus or the local area from the lower side of the anus. Therefore, only the exposed portion can be cleaned, and the inside of the colon or the vagina cannot be cleaned.

In addition, the conventional bidet device uses the water supplied through a tap water pipe without purifying the same. Therefore, there is a problem that the degree of cleanliness is low.

In order to solve the above problems, the present applicant has developed various types of bidet devices capable of being connected to a shower hose to supply purified water, for which the present applicant has filed Korean patent applications as follows.

Korean patent application 1 discloses a purified water discharge type bidet device for purifying and discharging water supplied from the outside so as to clean an anus or a vagina, including: a water purification housing for purifying water introduced through a water inlet formed at the lower end thereof; a main body housing positioned above the water purification housing and provided with a vibrator installed therein; a bidet housing coupled to an upper surface and a rear surface of the main body housing and provided with a battery installed therein on the rear surface side thereof; a water supply hose installed inside the main body housing and configured to supply the water of the water purification housing to the bidet housing through a water outlet of the main body housing; a water quantity/pressure regulation member installed at the main body housing and configured to regulate a flow rate of discharged water by changing a cross-sectional area of the water supply hose; an antibacterial silicone vibration penetrator installed at a water outlet of the bidet housing and configured to spray purified water through a nozzle at a tip portion thereof inserted into a vagina or a colon; and a connecting pin for connecting the vibrator and the antibacterial silicone vibration penetrator.

Korean patent application 2 discloses a bidet device provided with a water purifier, including: an introduction hose for introducing cleaning water; a water purifier including a purification chamber having an inlet connected to the introduction hose to introduce the cleaning water and an outlet configured to discharge the cleaning water introduced through the inlet, and a filter element accommodated in the purification chamber so as to purify the cleaning water introduced into the purification chamber; a head removably coupled to the water purifier and having a cleaning water discharge port connected to the outlet of the purification chamber; a bidet nozzle detachably coupled to the head and configured to discharge water from the discharge port; a control valve configured to selectively cut off the washing water supplied to the discharge port of the head and to regulate the flow rate and pressure of the cleaning water; and a post-treatment filter configured to secondarily purify the cleaning water that has passed through the filter element of the purification chamber. The bidet device can carry out cleaning as the bidet device is brought close to a portion requiring cleaning by a hand, can clean any portion of a human body, can insert the antibacterial silicone hose into the colon or the vagina to effectively clean the inside of the colon or the vagina, can effectively clean an area to be cleaned by using the cleaning water after purifying the same, and can prevent the inflow of contaminants into the human body.

Korean patent application 3 discloses a bidet beauty mechanism provided with a vibration device, including: an introduction hose configured to introduce cleaning water; a water purifier connected to the introduction hose and configured to purify the introduced cleaning water; a head detachably coupled to the water purifier and having an open tip portion communicating with the water purifier; a control valve configured to selectively shut off the cleaning water supplied to the open tip portion of the head or to regulate the flow rate and pressure of the cleaning water; a tip operation unit detachably coupled to the open tip portion of the head; and a vibration device installed on the head so as to be operatively connected to the tip operation unit. The bidet insertion device as a tip operation unit includes: a main body detachably coupled to the open tip portion of the head; an antibacterial silicone hose extending long forward of the main body so as to be inserted into a user's colon or vagina and having a flow path communicating with the open tip portion of the head and a nozzle head configured to spray the cleaning water introduced through the flow path; and a vibration bar inserted into the flow path of the antibacterial silicone hose and configured to transmit the vibration of the vibration device to the antibacterial silicone hose. The bidet beauty mechanism can clean any portion of a human body, can clean the inside of the colon or the vagina, and can maximize the cleaning effect by performing cleaning with vibrated cleaning water.

Korean patent application 4 discloses a hose connection type bidet device, including: a bidet head having a discharge tube installed therein; a bidet nozzle detachably coupled to a tip of the bidet head; a water purifier coupled to a lower end of the bidet head; and a control valve coupled to an inlet of the water purifier to control the supply of water to the water purifier. The purifier includes: a filter including a purification tube, a purifying material powder contained in the purification tube, a post-treatment filter installed at an outlet of the purification tube and a leakage preventing grill installed at an inlet of the purification tube; and a water purifier housing configured to accommodate the filter therein. The bidet device can prevent the water flowing down during the cleaning of the anus or the local area from reaching the hand, can assure easy operation of the control valve, and can make it possible to easily replace the filter for purifying the water.

Korean patent application 5 discloses a colon cleaning medical device, including: a head bent in a predetermined shape and having a discharge tube installed therein; an antibacterial silicone hose coupled to a tip of the head so as to communicate with an outlet of the discharge tube and configured to be inserted into a colon of a human body; a fitting member provided with a fitting protrusion and disposed between the antibacterial silicone hose and the head to maintain airtightness of the antibacterial silicone hose; a rubber member provided with an engagement protrusion for partially surrounding the fitting member; a water purifier coupled to a lower end of the head to supply purified water to the discharge tube; and a control valve coupled to an inlet of the water purifier to control the supply of water from a water supply hose to the water purifier. The water purifier includes: a filter including a purification tube connected to an outlet of the control valve and an inlet of the discharge tube, a purifying material powder contained in the purification tube, a post-treatment filter installed at an outlet of the purification tube and a leakage preventing grill installed at an inlet of the purification tube to prevent leakage of the purifying material powder; and a water purifier housing configured to accommodate the filter therein and detachably coupled to the head and the control valve.

However, the above-mentioned conventional bidet device or colon-cleaning medical device has a disadvantage in that it is difficult to thoroughly purify tap water and it is impossible to visually confirm the contamination of the filter installed in the head part.

Furthermore, since the control valve for regulating the water pressure is provided in the body part, there is a problem that the water flowing down when cleaning the anus or the local area may contaminate the hand.

In addition, there is a problem that water leakage may occur at the connection portion connecting the shower hose and the body part.

SUMMARY

In view of the aforementioned problems inherent in the related art, it is an object of the present invention to provide a medical device capable of converting tap water into functional water, filtering and discharging the functional water, maintaining the inside of a colon and a vagina, an anus and a local area clean, and giving help to the health of a user.

Another object of the present invention is to provide a medical device capable of cleaning the inside of a colon and a vagina with one device and being used as an ordinary bidet device or a shower device.

A further object of the present invention is to provide a medical device capable of magnetizing cleansing water with a strong magnet and supplying the magnetized cleaning water so that a body function is activated by the magnetized cleaning water.

A still further object of the present invention is to provide a medical device capable of making it possible to visually confirm the degree of contamination of a filter member.

A yet still further object of the present invention is to provide a medical device capable of preventing the water used during cleaning from contaminating a hand and improving cleanliness.

An even yet still further object of the present invention is to provide a medical device capable of being easily connected to a shower hose, being used in a portable manner, and making it possible to easily operate an operation knob of an operation unit for regulating a water pressure.

An additional even yet still further object of the present invention is to provide a medical device capable of preventing water from being leaked from between valve housing and valve spool and preventing the valve spool from being freely rotated.

According to one embodiment of the present invention, there is provided a medical device for constipation prevention, coprostasis removal and good bowel movement, including: a hollow body part formed in a predetermined bent shape; a head part provided at a tip portion thereof with a discharge port for discharging cleaning water and detachably coupled to a front end of the body part; a connection part connected to a shower hose and a rear end of the body part and provided with a control valve for controlling water supply, a water flow rate and a water pressure; a water purification tube built in the body part and provided with leakage preventing grilles at both ends thereof; and a purified water discharge part provided inside the head part and configured to remove foreign substances in water by using a filter, wherein germanium balls, tourmaline balls and antibacterial crystal balls are sequentially stacked in the water purification tube, and at least one magnetization ring made of a neodymium magnet is assembled to an outer circumferential surface of the water purification tube.

In the medical device, the connection part may include a control valve for controlling water supply, a water flow rate and a water pressure, and a spherical valve cap for protecting the control valve, and the control valve may include: a spherical valve housing having a lower end thread portion fastened to the shower hose, an upper end thread portion fastened to the leakage preventing grill of the water purification tube and a hollow portion formed inside the control valve; a valve spool inserted into the valve housing and having an opening degree adjustment hole formed in a radial direction so that an opening degree of the hollow portion of the valve housing is changed according to a rotation angle of the valve spool; an operation knob coupled to the valve spool protruding outside the valve housing; and a sealing member provided outside the valve cap to prevent water leakage in the valve housing.

In the medical device, the valve spool may include: a spool body having a through hole formed in the radial direction and a protrusion formed on an outer circumferential surface thereof, the spool body press-fitted into the valve housing; and a connection member for connecting the operation knob and the spool body.

In the medical device, the body part may be divided into segments along a bending direction center line, and each of the segments may be formed through three-dimensional molding.

The medical device may further include: a vibration device provided at an upper end of the body part to vibrate the filter member, wherein the vibration device is connected to the filter member via a vibration bar.

In the medical device, the filter member may be composed of a filter for removing foreign substances and a filter case made of a transparent material and configured to accommodate the filter therein, and a sight window for visually confirming a contamination state of the filter member may be formed on one side of the head part.

In the medical device, the discharge port of the head part may be formed in a gull shape.

In the medical device, a connection member selected from a group consisting of an intestine cleaning nozzle, a vagina cleaning nozzle, a cleaning cap and a shower head may be connected to a tip of the head part.

With the medical device for constipation prevention, coprostasis removal and good bowel movement according to the present invention, the cleaning water is converted into functional water through the use of germanium balls, tourmaline balls and antibacterial crystal balls accommodated in the water purification tube, sterilized, filtered and discharged. This makes it possible to supply cleaning water from which various foreign substances and bacteria have been removed.

Furthermore, since the magnetization ring made of a neodymium magnet having a strong magnetic force is provided in the water purification tube to magnetize the cleaning water, it is possible to improve the sterilizing effect.

Furthermore, if the intestine-cleaning nozzle is coupled to the tip of the head part and inserted into the intestine, it is possible to remove the aspiration accumulated in the colon as the intestine wall extending from the rectum to the membrane is tapped by a strong water stream. The makes it possible to easily perform enema. Accordingly, it is possible to solve the inconvenience of visiting a hospital for colon cleaning and enema.

Furthermore, since the pulsating cleaning water is injected into the colon to smoothly stimulate the colon, it is possible to prevent constipation and to induce good bowel movement.

In particular, since the intestines can be cleaned without using electric stimulation or chemical solutions, it is possible to easily clean the intestine at home without imposing a burden on the human body.

Furthermore, if the vagina cleaning nozzle is coupled to the tip of the head part and then inserted into the vagina, it is possible to prevent generation of odor and to remove bacteria present in the vagina, thereby preventing female diseases.

Furthermore, if the cleaning cap is coupled to the tip of the head part and used as a bidet device, it is possible to completely clean the inside of the anus, thereby preventing the feeling of remnant excrement.

Furthermore, if the shower head is coupled to the tip of the head part and used as an ordinary shower device, it is possible to clean the waste materials in the pores of the skin with the clear and clean magnetized water, thereby keeping the skin smooth and preventing the formation of various bacteria.

Furthermore, since the control valve is provided at the connection portion connected to the shower hose, the water used for cleaning is not adhered to the hand, thereby improving the cleanliness.

Furthermore, since the protrusion is formed on the outer circumferential surface of the valve spool of the control valve and press-fitted into the valve housing, no leakage occurs between the valve spool and the valve housing, and the opening degree of the valve housing set by the operation knob can be maintained.

Furthermore, as the body part is divided into segments along the bending direction center line and each of the segments is formed by three-dimensional molding, it is possible to easily assemble the body part and to make the body part more beautiful.

Furthermore, since the vibration device is provided on the body part to vibrate the filter member, the cleaning water is vibrated to maximize the cleaning effect.

In addition, since the filter case of the filter member is formed of a transparent material and the sight window is formed on the head part, the contamination state of the filter can be checked without removing the head part, and the filter can be replaced in a timely manner.

BRIEF DESCRIPTION OF THE DRAWINGS

FIG. 1 is a partially exploded perspective view of a medical device for constipation prevention, coprostasis removal and good bowel movement according to the present invention.

FIG. 2 is a sectional view of the medical device for constipation prevention, coprostasis removal and good bowel movement according to the present invention.

FIG. 3 is a view showing a connection member connected to the medical device for constipation prevention, coprostasis removal and good bowel movement according to the present invention.

FIG. 4 is a sectional view of a purified water discharge portion according to the present invention.

FIG. 5 is an enlarged perspective view of a head part according to the present invention.

FIG. 6 is an exploded perspective view showing a state in which a body part according to the present invention is exploded.

FIG. 7 is a sectional view showing an internal structure of a water purification tube according to the present invention.

FIG. 8 is a sectional view showing an internal structure of a connection part according to the present invention.

DETAILED DESCRIPTION

A preferred embodiment of a medical device for constipation prevention, coprostasis removal and good bowel movement according to the present invention will now be described in detail with reference to the accompanying drawings.

Referring to FIGS. 1 to 8, the medical device for constipation prevention, coprostasis removal and good bowel movement includes a body part 10, a head part 20 and a connection part 30.

The body part 10 is a hollow structure formed in a predetermined bent shape. As shown in FIG. 7, a water purification tube 15 having germanium balls 15a, tourmaline balls 15b and antibacterial crystal balls 15c sequentially stacked therein and provided with leakage preventing grilles 16 and 17 at both ends thereof is installed in the body part 10.

Furthermore, at least one magnetization ring 18 made of a Neodymium magnet is coupled to the outer circumferential surface of the water purification tube 15.

The germanium balls 15a, the tourmaline balls 15b and the antibacterial crystal balls 15c may convert tap water into clear clean cleaning water which may be converted into functional magnetized water by the magnetization ring 18.

The germanium balls 15a provided inside the body part 10 removes harmful metal ions and impurities such as calcium carbonate, magnesium and lime salt contained in tap water, and converts the tap water into healthy water such as phreatic water or the like which is beneficial to the human body.

The tourmaline balls 15b provided inside the body part 10 generates a large amount of negative ions that makes the human body active while emitting energy semi-permanently.

In addition, the antibacterial crystal balls 15c provided inside the body part 10 provide antimicrobial activity and generate negative ions and far-infrared rays for a long time.

Accordingly, when the tap water passes through the water purification tube 15, harmful metal ions or impurities are removed from the tap water, whereby the tap water is converted into functional water which contains a large amount of negative ions and far-infrared rays and which exhibits excellent antibacterial activity.

The neodymium magnet has the strongest magnetic force on the earth. Therefore, if the magnetization ring 18 is formed by the neodymium magnet, it is possible for the strong magnetic energy to remove active oxygen in the water and to improve the sterilizing effect.

As shown in FIG. 6, the water purification tube 15 may be made of PVC or silicone, and may be deformably formed so that the water purification tube 15 can be easily attached inside the body part 10 bent in a predetermined shape.

Furthermore, it is preferable that the body part 10 is divided into segments 10a and 10b along the bending direction center line and each of the segments 10a and 10b is formed through three-dimensional molding.

Accordingly, it is possible to form the body part 10 in a beautiful curved shape.

It is also preferable that the divided surface of the connection part 30 is formed to be the same as the divided surface of the body part 10.

As shown in FIG. 1, it is preferable that a vibration device 11 for vibrating a filter 26a of a filter member 26 is further provided at the upper end of the body part 10.

The vibration device 11 is connected to the filter member 26 by a vibration bar 12 to vibrate the filter member 26 to generate waves in the cleaning water, thereby enhancing the cleaning effect of the cleaning water.

The head part 20 is provided at the tip thereof with a discharge port 21 for discharging the cleaning water and is detachably coupled to the tip of the body part 10. A purified water discharge part 25 for removing foreign substances in the water using the filter 26a is provided in the head part 20.

As shown in FIG. 4, the purified water discharge part 25 includes a filter member 26 for removing foreign substances through the use of a filter. The lower end portion of the purified water discharge part 25 is fastened to the leakage preventing grill 16 provided at the upper end of the water purification tube 15.

The filter member 26 is composed of a filter for removing foreign substances and a filter case made of a transparent material and configured to accommodate the filter therein. A sight window 22 for confirming the contamination state of the filter member 26 is formed on one side of the head part 20.

Thus, it is possible to visually confirm the contamination of the filter through the sight window 22 without removing the filter member 26 from the head part 20.

As shown in FIG. 6, the head part 20 is divided into a front body 20a provided with a discharge port 21 and configured to form a front portion of the head part 20, and a rear body 20b configured to form a rear portion of the head part 20 and coupled to the front body 20a. The sight window 22 is formed on the rear body 20b.

It is preferable that, as shown in FIG. 5, the discharge port 21 of the head part 20 is formed in a gull shape. The gull-shaped discharge port 21 allows the cleaning water to be sprayed rhythmically so as to clean the local area or the anus.

As shown in FIG. 3, a connection member 24 such as an intestine cleaning nozzle 24a, a vagina cleaning nozzle 24b, a cleaning cap 23 or a shower head 24c is selectively connected to the tip of the head part 20. A coupling portion that can be coupled to the tip of the head part 20 is provided at the rear end portion of the connection member 24.

In order to clean the colon, the intestine cleaning nozzle 24a is coupled to the tip of the head part 20 and inserted into the intestine. In order to clean the vagina, the vagina cleaning nozzle 24b is coupled to the tip of the head part 20 and inserted into the vagina.

The intestine cleaning nozzle 24a and the vagina cleaning nozzle 24b are made of a silicone material and may be smoothly inserted into the colon or the vagina. As shown in FIG. 3. a large number of spray holes are formed at the tip portion of each of the intestine cleaning nozzle 24a and the vagina cleaning nozzle 24b.

In addition, when it is desired to use the medical device as an ordinary bidet for cleaning the anus or the local area, as shown in FIG. 1, the cleaning cap 23 is coupled to the tip of the head part 20. When it is desired to use the medical device as a shower device, the shower head 24c is coupled to the tip of the head part 20.

The connection part 30 is configured to connect the shower hose 50 and the body part 10. As shown in FIG. 2, the connection part 30 includes a control valve for controlling the supply of water, the flow rate of water and the pressure of water, and a spherical valve cap 35 for protecting the control valve.

As shown in FIG. 8, the control valve includes: a spherical valve housing 31 having a lower end thread portion 31a fastened to the shower hose 50, an upper end thread portion 31b fastened to the leakage preventing grill 17 of the water purification tube 15 and a hollow portion 31c formed inside the control valve; a valve spool 32 inserted into the valve housing 31 and having an opening degree adjustment hole formed in a radial direction so that an opening degree of the hollow portion 31c of the valve housing 31 is changed according to a rotation angle of the valve spool 32; an operation knob 33 coupled to the valve spool 32 protruding outside the valve housing 31; and a sealing member 34 provided outside the valve cap 35 to prevent water leakage in the valve housing 31.

The valve spool 32 includes: a spool body 32a having a through hole 32b formed in the radial direction and a protrusion formed on an outer circumferential surface thereof, the spool body 32a press-fitted into the valve housing 31; and a connection member 32c for connecting the operation knob 33 and the spool body 32a.

Accordingly, if the valve spool 32 is rotated using the operation knob 33, the opening degree of the valve housing 31 is kept constant by the pressing force of the spool body 32a. Thus, water leakage does not occur between the valve housing 31 and the valve spool 32.

Hereinafter, the operation and effect of the medical device for constipation prevention, coprostasis removal and good bowel movement according to the present invention will be described.

If the lower end thread portion 31a of the connection part 30 is fastened to the shower hose 50 connected to a tap water pipe and then the tap water pipe is opened, water is introduced into the shower hose 50.

In this state, if the hollow portion 31c of the valve housing 31 is opened by rotating the operation knob 33 constituting the control valve of the connection part 30, the water in the shower hose 50 is supplied to the water purification tube 15 in the body part 10 through the connection part 30.

At this time, the protrusion formed on the outer circumferential surface of the valve spool 32 inserted into the valve housing 31 is press-fitted into the valve housing 31. Therefore, the water is not leaked from between the valve housing 31 and the valve spool 32. The opening degree of the valve housing 31 determined by rotating the operation knob 33 is maintained.

Various kinds of impurities contained in the water supplied to the water purification tube 15 are removed by the germanium balls 15a, the tourmaline balls 15b and the antibacterial crystal balls 15c, whereby the water is converted into cleaning water which contains a large amount of negative ions and far-infrared rays and which exhibits excellent antibacterial activity.

Thereafter, the cleaning water of the water purification tube 15 is filtered by the filter 26a of the filter member 26 after flowing into the purified water discharge part 25, and is then discharged through the discharge port 21 of the head part 20.

At this time, vibration is generated by the vibration device 11 provided on the tip side of the water purification tube 15 and is transmitted to the filter member 26 through the vibration bar 12.

As a result, the cleaning water passing through the filter member 26 generates waves, thereby improving the cleaning effect.

When the intestine is to be cleaned, the intestine cleaning nozzle 24a is coupled to the tip of the head part 20 and inserted into the colon.

When the vagina is to be cleaned, the vagina cleaning nozzle 24b is coupled to the tip of the head part 20 and inserted into the vagina.

In order to use the medical device as an ordinary bidet, the cleaning cap 23 is coupled to the tip of the head part 20.

In order to use the medical device as an ordinary shower device, the showerhead 24c is coupled to the tip of the head part 20.

While a preferred embodiment of the present invention have been described above, the present invention is not limited to the above-described embodiment. Various modifications and changes may be made without departing from the scope and spirit of the present invention defined in the claims.

What is claimed is:

1. A medical device for constipation prevention, coprostasis removal and good bowel movement, comprising:
    a hollow body part formed in a predetermined bent shape;
    a head part provided at a tip portion thereof with a discharge port for discharging cleaning water and detachably coupled to a front end of the body part;
    a connection part connected to a shower hose and a rear end of the body part and provided with a control valve for controlling water supply, a water flow rate and a water pressure;
    a water purification tube the positioned within hollow body part and provided with leakage preventing grilles at both ends thereof; and
    a purified water discharge part provided inside the head part and including a filter member configured to remove foreign substances in water flowing therethrough,
    wherein germanium balls, tourmaline balls and antibacterial crystal balls are sequentially stacked in the water purification tube, and
    at least one magnetization ring made of a neodymium magnet and mounted upon an outer circumferential surface of the water purification tube.

2. The medical device of claim 1, wherein the connection part includes a spherical valve cap for protecting the control valve, and the control valve includes:
    a spherical valve housing having a lower end thread portion fastened to the shower hose, an upper end thread portion fastened to one of the leakage preventing grills of the water purification tube and a hollow portion formed inside the control valve;
    a valve spool inserted into the valve housing and having an opening degree adjustment hole formed in a radial direction so that an opening degree of the hollow portion of the valve housing is changed according to a rotation angle of the valve spool;
    an operation knob coupled to the valve spool protruding outside the valve housing; and
    a sealing member provided outside the valve cap to prevent water leakage in the valve housing.

3. The medical device of claim 2, wherein the valve spool includes:
    a spool body having a through hole formed in the radial direction and a protrusion formed on an outer circumferential surface thereof, the spool body press-fitted into the valve housing; and
    a connection member for connecting the operation knob and the spool body.

4. The medical device of claim 1, wherein the body part is divided into segments along a bending direction center line, and each of the segments is formed through three-dimensional molding.

5. The medical device of claim 1, further comprising:
    a vibration device provided at an upper end of the body part to vibrate the filter member,
    wherein the vibration device is connected to the filter member via a vibration bar.

6. The medical device of claim 1, wherein the filter member comprising of a filter for removing foreign substances and a filter case made of a transparent material and configured to accommodate the filter therein, and a sight window for visually confirming a contamination state of the filter member is formed on one side of the head part.

7. The medical device of claim 1, wherein the discharge port of the head part is formed in a gull shape.

8. The medical device of claim 1, wherein a connection member selected from a group consisting of an intestine cleaning nozzle, a vagina cleaning nozzle, a cleaning cap and a shower head is connected to a tip of the head part.

* * * * *